(12) United States Patent
Koehler et al.

(10) Patent No.: US 9,287,017 B2
(45) Date of Patent: Mar. 15, 2016

(54) DIFFERENTIAL PHASE-CONTRAST IMAGING WITH INCREASED DYNAMIC RANGE

(75) Inventors: Thomas Koehler, Norderstedt (DE); Ewald Rössl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 271 days.

(21) Appl. No.: 13/983,063

(22) PCT Filed: Feb. 2, 2012

(86) PCT No.: PCT/IB2012/050484
§ 371 (c)(1),
(2), (4) Date: Aug. 1, 2013

(87) PCT Pub. No.: WO2012/107862
PCT Pub. Date: Aug. 16, 2012

(65) Prior Publication Data
US 2013/0308751 A1 Nov. 21, 2013

(30) Foreign Application Priority Data
Feb. 7, 2011 (EP) .................................... 11153480

(51) Int. Cl.
*G03H 5/00* (2006.01)
*G21K 1/06* (2006.01)
*A61B 6/00* (2006.01)
*A61B 6/04* (2006.01)

(52) U.S. Cl.
CPC .............. *G21K 1/067* (2013.01); *A61B 6/4035* (2013.01); *A61B 6/4291* (2013.01); *A61B 6/484* (2013.01); *G21K 1/06* (2013.01); *A61B 6/0407* (2013.01); *A61B 6/4078* (2013.01); *A61B 6/4441* (2013.01); *A61B 6/508* (2013.01); *G21K 2201/067* (2013.01); *G21K 2207/005* (2013.01)

(58) Field of Classification Search
CPC .... A61B 6/4035; A61B 6/4291; A61B 6/484; G21K 1/06; G21K 1/062
See application file for complete search history.

(56) References Cited

U.S. PATENT DOCUMENTS

| 7,639,786 B2 * | 12/2009 | Baumann et al. ............. 378/145 |
| 2007/0153979 A1 | 7/2007 | Baumann et al. |
| 2007/0183579 A1 | 8/2007 | Baumann et al. |

FOREIGN PATENT DOCUMENTS

| CN | 101011256 A | 8/2007 |
| DE | 102006037281 | 8/2007 |
| WO | WO2004071298 | 8/2004 |
| WO | WO2009113726 | 9/2009 |
| WO | 2010146503 A1 | 12/2010 |

* cited by examiner

*Primary Examiner* — Courtney Thomas

(57) ABSTRACT

In X-ray differential phase-contrast imaging. In order to enhance the information acquired by phase-contrast imaging, an analyzer grating (34) is provided with an absorption structure (48). The latter includes a first plurality (50) of first areas (52) with a first X-ray attenuation, and a second plurality (54) of second areas (56) with a second X-ray attenuation. The second X-ray attenuation is smaller than the first X-ray attenuation, and the first and second areas are arranged periodically in an alternating manner. A third plurality (58) of third areas (60) is provided with a third X-ray attenuation, which lies in a range from the second X-ray attenuation to the first X-ray attenuation, wherein every second of the first or second areas is replaced by one of the third areas.

13 Claims, 11 Drawing Sheets

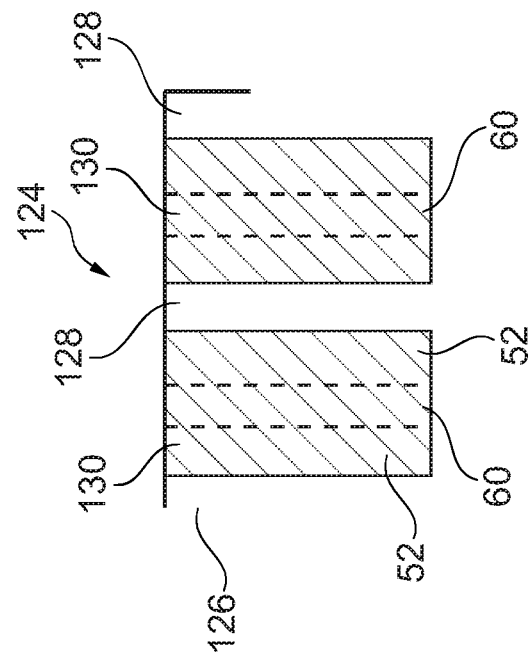
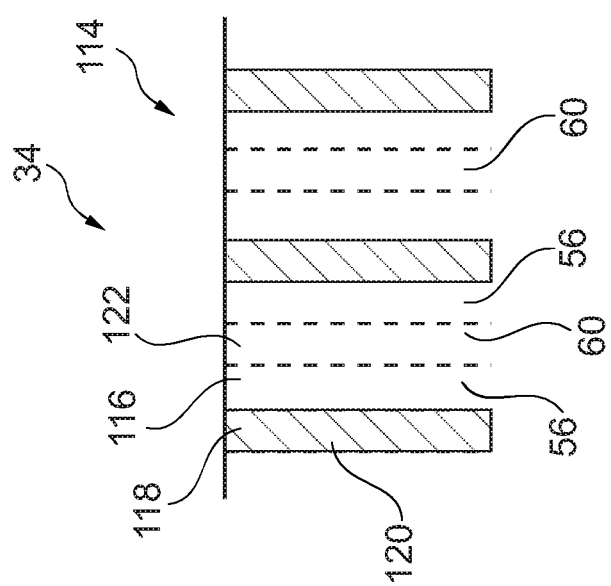

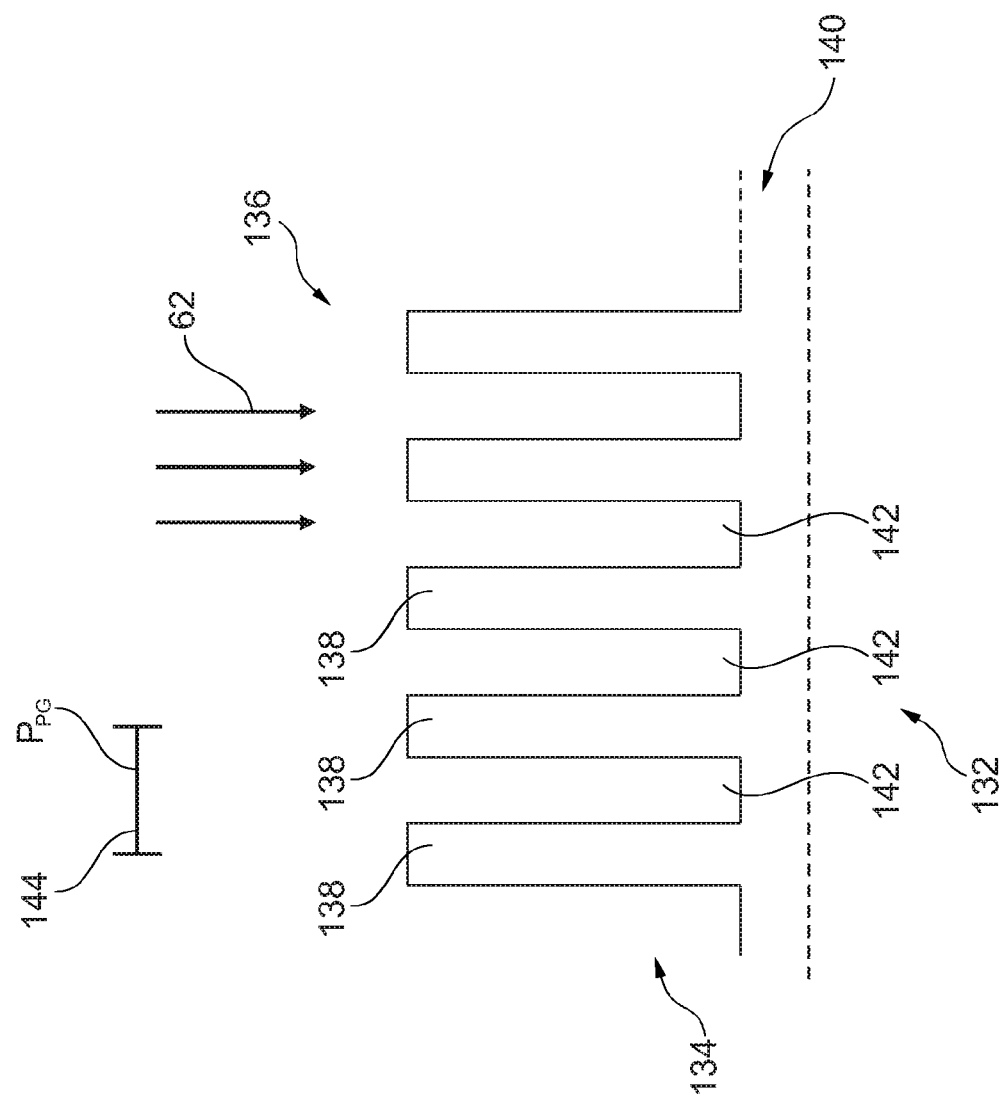

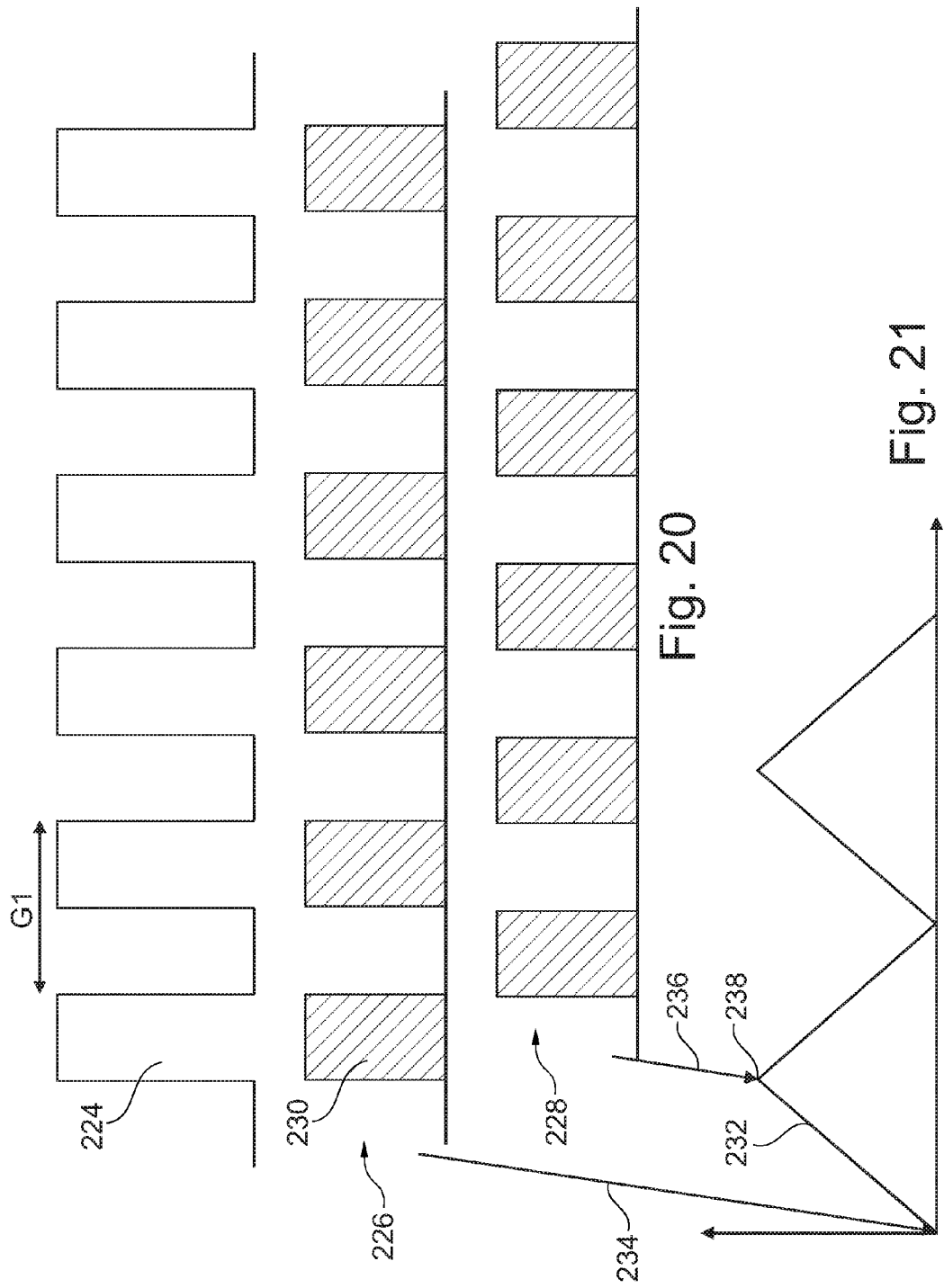

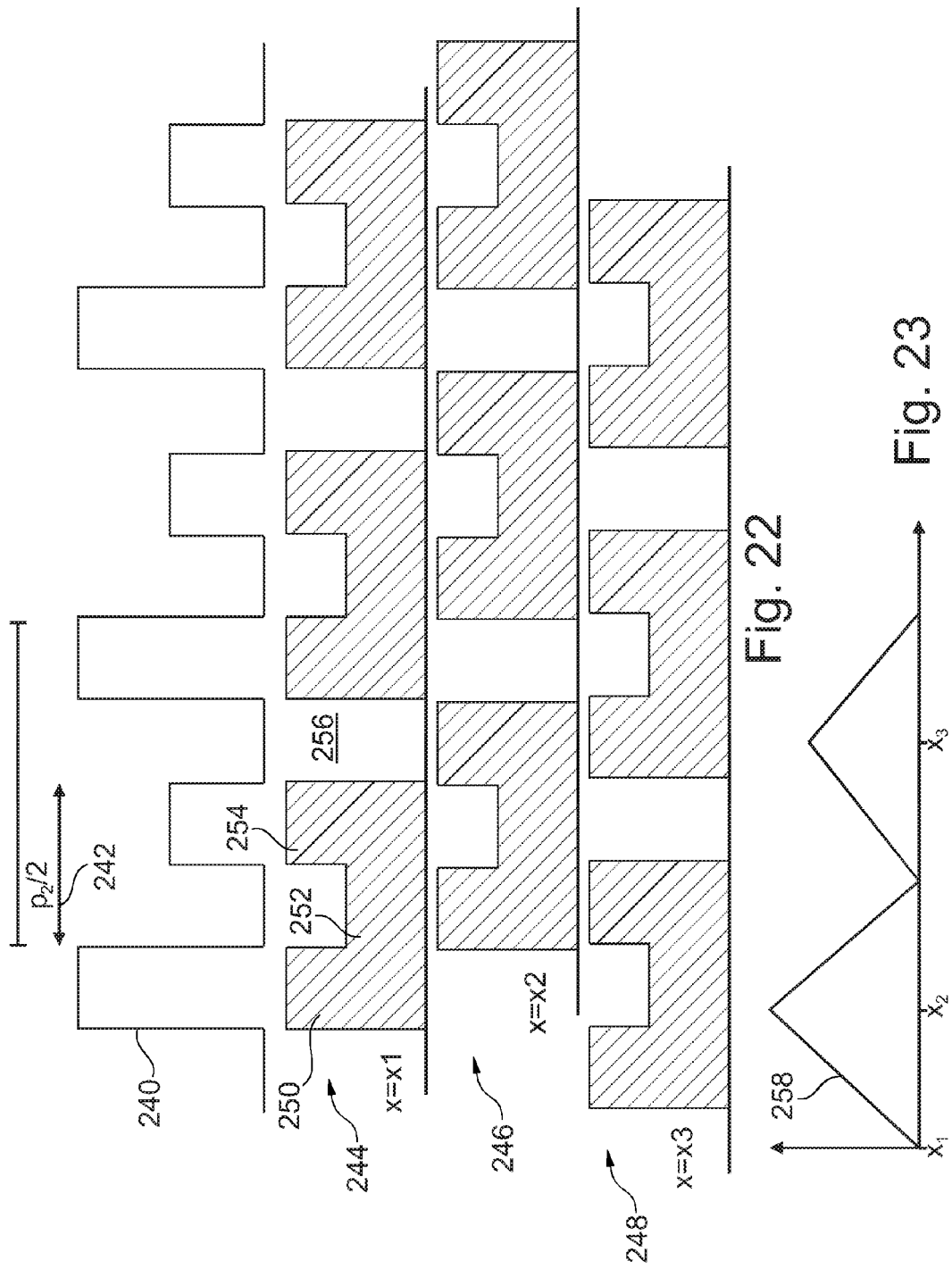

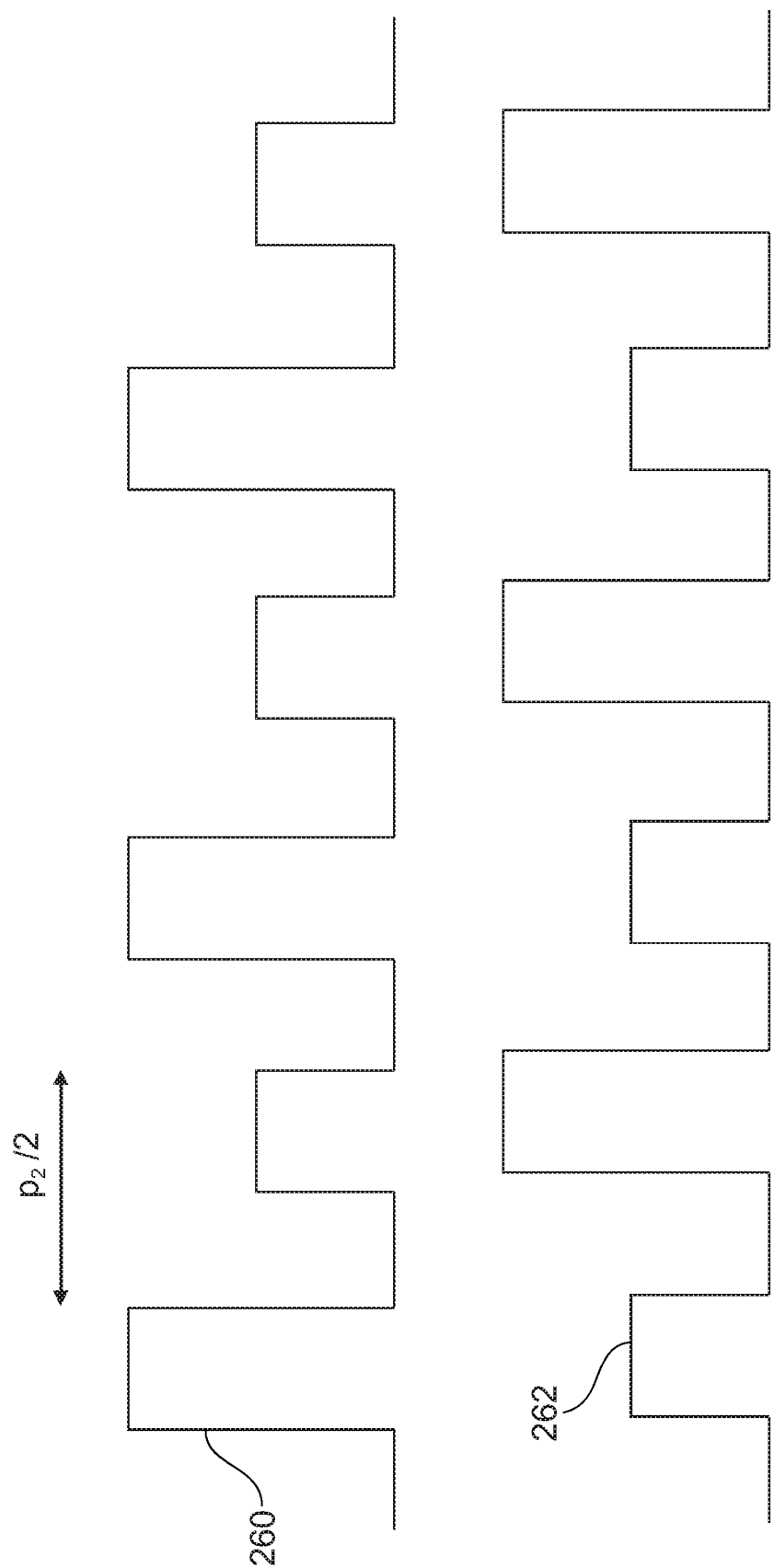

DIFFERENTIAL PHASE-CONTRAST IMAGING WITH INCREASED DYNAMIC RANGE

CROSS-REFERENCE TO PRIOR APPLICATIONS

This application is the U.S. National Phase application under 35 U.S.C. §371 of International Application Serial No. PCT/IB2012/050484, filed on Feb. 2, 2012, which claims the benefit of European Application Serial No. 11153480.6, filed on Feb. 7, 2011. These applications are hereby incorporated by reference herein.

FIELD OF THE INVENTION

The present invention relates to an analyzer grating for X-ray differential phase-contrast imaging, a phase grating for X-ray differential phase-contrast imaging, a detector arrangement of an X-ray system, an X-ray image acquisition device, and an X-ray imaging system for differential phase-contrast imaging, and a method for differential phase-contrast imaging as well as a computer program element and a computer-readable medium.

BACKGROUND OF THE INVENTION

Differential phase-contrast imaging is used to enhance contrast of low absorbing specimen, compared to conventional amplitude contrast images, for example. In WO 2004/071298 A1, an apparatus is provided for generating phase-contrast X-ray image, which comprises, along an optical path, an incoherent X-ray source, a first beam splitter grating, a second beam recombiner grating, an optical analyzer grating and an image detector. In differential phase-contrast imaging, the grating G1, i.e. the so-called phase grating, is typically a pure phase grating with a pitch G1 that imposes a phase shift onto the phase front of the coherent X-ray radiation. After further propagation of the wave front to the analyzer grating G2 with a pitch in the order of G2=½G1, the intensity of the beam is modulated with a period equal to G2. Using an analyzer grating that has a modulation of its transmission with this pitch, the detector signal behind the analyzer grating has a periodicity of G2 and the phase of the signal can be used to derive position of the intensity maxima and thus the gradient of the phase front.

SUMMARY OF THE INVENTION

However, it has been shown that in particular for large objects, the above described grating-based setup has a limited dynamic range to phase gradients.

It is therefore an object of the present invention to enhance the information acquired by phase-contrast imaging.

The object of the present invention is solved by the subject-matter of the independent claims, wherein further embodiments are incorporated in the dependent claims.

It should be noted that the following described aspect and embodiments of the invention apply also for the analyzer grating, the phase grating, the detector arrangement, the X-ray image acquisition device, the X-ray imaging system, the method, the program element and the computer-readable medium.

According to a first aspect of the invention, an analyzer grating for X-ray differential phase-contrast imaging is provided which comprises an absorption structure with a first plurality of first areas with a first X-ray attenuation, and a second plurality of second areas with a second X-ray attenuation. The second X-ray attenuation is smaller than the first X-ray attenuation. The first and second areas are arranged periodically in an alternating manner. A third plurality of third areas is provided with a third X-ray attenuation, which lies in a range from the second X-ray attenuation to the first X-ray attenuation. Every second of the first or second areas is replaced by one of the third areas.

According to a further aspect, the first areas are X-ray opaque, the second areas are X-ray transparent, and the third areas have an X-ray attenuation that lies between the attenuation of the first and second areas.

According to a further aspect, a phase grating for X-ray differential phase-contrast imaging is provided, comprising a deflection structure with a fourth plurality of fourth areas and a fifth plurality of fifth areas, wherein the fourth and fifth areas are arranged periodically in an alternating manner. The fourth areas are provided to change the phase and/or amplitude of an X-ray radiation, and the fifth areas are provided to modulate the amplitude of the X-ray radiation.

According to a further aspect, a detector arrangement of an X-ray system for generating differential phase-contrast images of an object is provided, comprising a phase grating, an analyzer grating, and a detector with a sensor adapted to record radiation intensity variations of an X-ray radiation. In radiation direction, i.e. along an optical path, the analyzer grating is arranged behind the phase grating, and the detector is arranged behind the analyzer grating. The phase grating is provided with a fourth plurality of fourth areas and a fifth plurality of fifth areas, wherein the fourth areas are provided to change the phase and/or amplitude of an X-ray radiation. The fourth and fifth areas are arranged periodically in an alternating manner with a phase grating pitch $p_{PG}$. Further, the analyzer grating is provided according to the above mentioned aspects or embodiments. The phase grating and/or the analyzer grating are adapted to be stepped in a manner transverse to the deflection structure at least over a full modulation period of the X-ray radiation passing the phase grating.

According to a further aspect, an image acquisition device for generating differential phase-contrast images of an object is provided with an X-ray source, a phase grating, an analyzer grating, and a detector. The X-ray source generates X-ray radiation and the image acquisition device is adapted to provide an X-ray beam with sufficient coherence, so that interference can be observed at the location of the analyzer grating. The phase grating, the analyzer grating, and the detector are provided as a detector arrangement according to the above mentioned embodiment.

According to a further aspect, an X-ray image system for differential phase-contrast imaging is provided, comprising an X-ray image acquisition device for generating differential phase-contrast images of an object according to the above mentioned embodiment, a processing unit, and an interface unit. The processing unit is adapted to control the X-ray source as well as the phase-stepping of the analyzer grating and/or the phase grating. The interface unit is adapted to provide the detected raw image data to the processing unit.

According to a further aspect, a method for differential phase-contrast imaging is provided, comprising the steps of:
a) applying at least partly coherent X-ray radiation to an object of interest;
b) applying the X-ray radiation passing the object to a phase grating recombining the splitted beams in an analyzer plane;
c) applying the recombined beams to an analyzer grating arranged in the analyzer plane;
d) recording raw image data with a sensor while stepping the analyzer grating;

wherein the phase grating in step b) is provided with a fourth plurality of fourth areas, and a fifth plurality of fifth areas, wherein the fourth areas are provided to change the phase and/or amplitude of an X-ray radiation, and wherein the fourth and fifth areas are arranged periodically in an alternating manner with a phase grating pitch $p_{PG}$. Further, in step b) a subharmonic in the interference pattern at the position of the analyzer grating is provided. The analyzer grating in step d) is an analyzer grating according to one of the above mentioned aspects or embodiments, and step d) comprises stepping the analyzer grating transversely over at least a full modulation period of the X-ray radiation passing the phase grating.

It can be seen as the gist of the invention to provide an analyzer grating, i.e. grating G2, in which every other intensity maximum is damped in relation to the preceding maximum, i.e. the first intensity maxima. As a result, in case of parallel X-ray propagation, the periodicity of the signal is no longer equal to ½G1, but equal to G1. Of course, in case of fan-like or fan-shaped propagating X-rays, the periodicities of current G2 gratings are in accordance with ½G1 depending on the magnification due to the fan-like propagation. The periodicities of G2 gratings of the invention are thus in accordance with G1 depending on the magnification due to the fan-like propagation. By changing the transmission of the analyzer grating such that it has a periodicity of G1, it is possible to detect a change in the intensity pattern. The maxima of the detected signal are the same but the depth of the minima differs since the maxima are attenuated differently. This increases the dynamic range of the phase gradient measurement significantly.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

FIGS. 11 and 12 show further embodiments of an analyzer grating according to the invention.

FIG. 13 shows a phase grating according to an embodiment of the invention.

FIG. 20 shows aspects of an ideal situation according to prior art.

FIG. 21 shows an intensity profile according to the ideal situation of FIG. 20.

FIG. 22 shows an aspect according to a further embodiment of the invention.

FIG. 23 shows a measured intensity according to the embodiment of FIG. 22.

FIG. 24 shows a further aspect of an embodiment according to the invention.

DETAILED DESCRIPTION OF EMBODIMENTS

Figure 1:
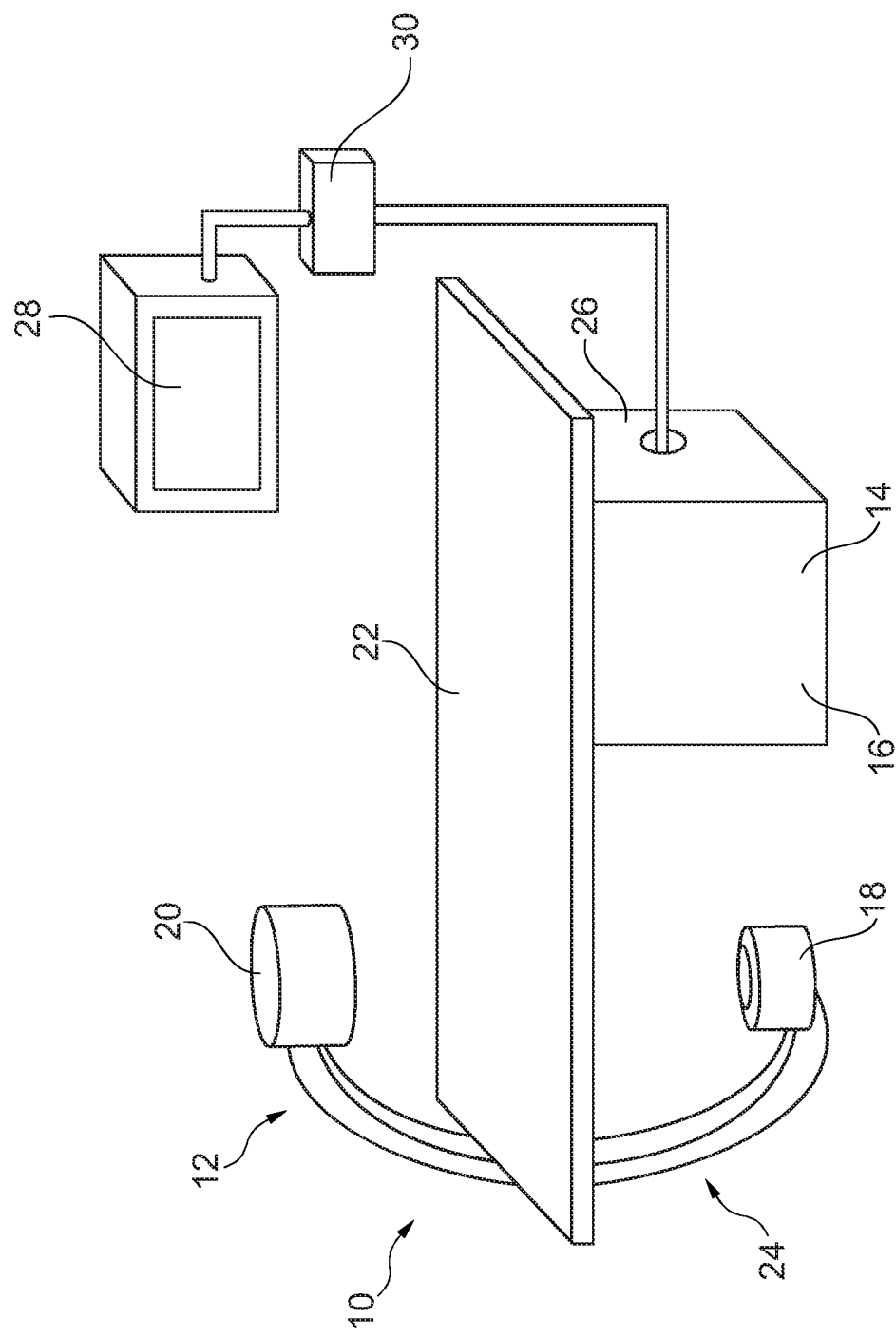
FIG. 1 schematically illustrates an X-ray imaging system according to the invention.

FIG. 1 schematically shows an X-ray imaging system 10 for differential phase-contrast imaging, comprising an X-ray image acquisition device 12 for generating differential phase-contrast images of an object according to one of the embodiments or aspects described below. The X-ray imaging system 10 further comprises a processing unit 14 and an interface unit 16 (not further shown). Further, the X-ray image acquisition device for generating differential phase-contrast images of an object comprises an X-ray source 18 and a detector arrangement 20 which is described with reference to FIG. 2 in the following below.

A table 22 is provided to receive a subject to be examined. The X-ray source and the detector arrangement 20 are mounted on a C-arm arrangement 24 such that the table 22 can be arranged between the X-ray source 18 and the detector arrangement 20. The C-arm arrangement 24 allows a movement of the X-ray image acquisition device 12 around the patient to be able to adapt the viewing direction. The table 22 is provided on a base 26 which is mounted to the floor of an examination room, for example. The base 26 comprises the processing unit 14 and the interface unit 16. Further, a display 28 is provided in the vicinity of the table 22 to provide information to the user. Further, a secondary interface unit 30 is arranged to provide the possibility to further control the system.

During the radiation procedure, a subject can be located between the source of X-ray radiation 12 and the detector arrangement 16. The latter is sending data to the processing unit 14 via the interface unit 16 to provide the detected raw image data to the processing unit. It must be noted that the processing unit 14 and the interface unit 16 can be provided also at other locations, also at different places, such as a different laboratory room or control room.

It is further noted that the example shown is of a so-called C-type X-ray image acquisition device. However, also other X-ray image acquisition devices can be provided, for example CT systems and stationary systems with fixed X-ray source and detector arrangement.

Figure 2:
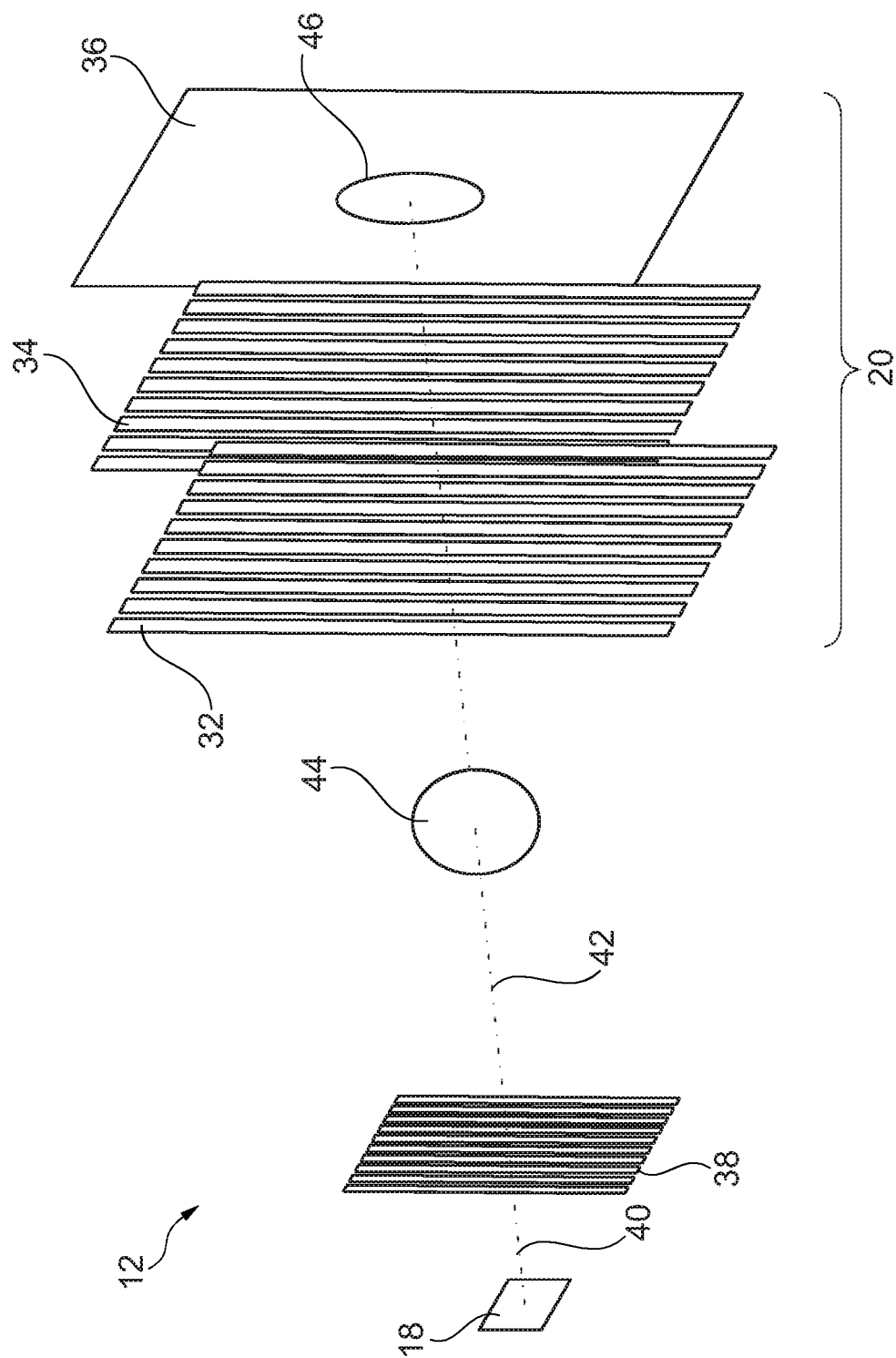
FIG. 2 illustrates an X-ray image acquisition device in a schematic setup with a detector arrangement according to an exemplary embodiment of the invention.

FIG. 2 schematically shows the detector arrangement 20 already mentioned in relation with FIG. 1. The detector arrangement 20 comprises a phase grating 32, an analyzer grating 34, and a detector 36 with a sensor adapted to record intensity variations of an X-ray radiation.

Further, the detector arrangement 20 is part of an X-ray image acquisition device 12, which has also already been mentioned above. The X-ray image acquisition device is schematically shown with the X-ray source 18, a source grating 38, and the phase grating 32, the analyzer grating 34 as well as the detector 36.

The X-ray source 18 is generating an X-ray beam 40 of polychromatic spectrum of X-rays. The source grating 38 is adapted to provide sufficient coherence to the X-ray beam passing the source grating, so that interference can be observed at the location of the analyzer grating 34. In other words, the X-ray beam 40 passes the source grating 38 and is then provided as an adapted X-ray beam 42.

According to a further embodiment, not shown, the source grating is omitted and the X-ray source is adapted to provide sufficient coherent X-ray radiation, so that interference can be observed at the location of the analyzer grating, for example by synchrotron or micro focus X-ray tubes. The latter could be used, for example, for animal screening.

As can be seen, the X-ray source 18, the source grating 38, the phase grating 32, the analyzer grating 34, and the detector 36 are arranged along an optical path. Further, FIG. 2 shows an object 44 which, for examination, is arranged between the source grating 38 and the phase grating 32.

On the detector 36, detectable image information 46 is schematically indicated.

The phase grating 32 will be explained further below with reference to FIG. 13. The analyzer grating 34 will be explained in the following with reference to FIGS. 3 to 12.

Figure 3:
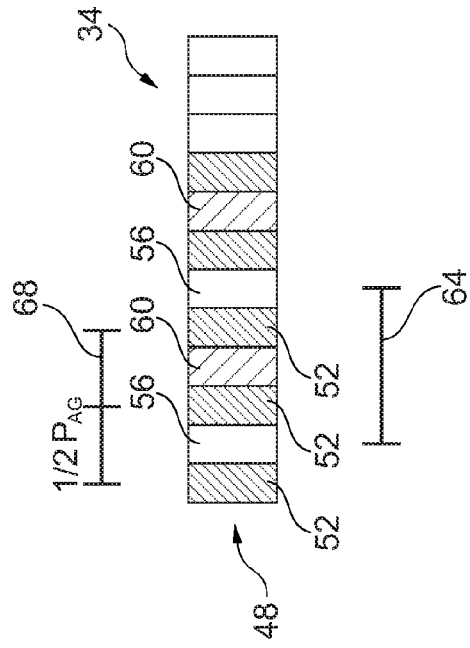
FIG. 3 schematically shows a first embodiment of an analyzer grating according to the invention.
Figure 4:
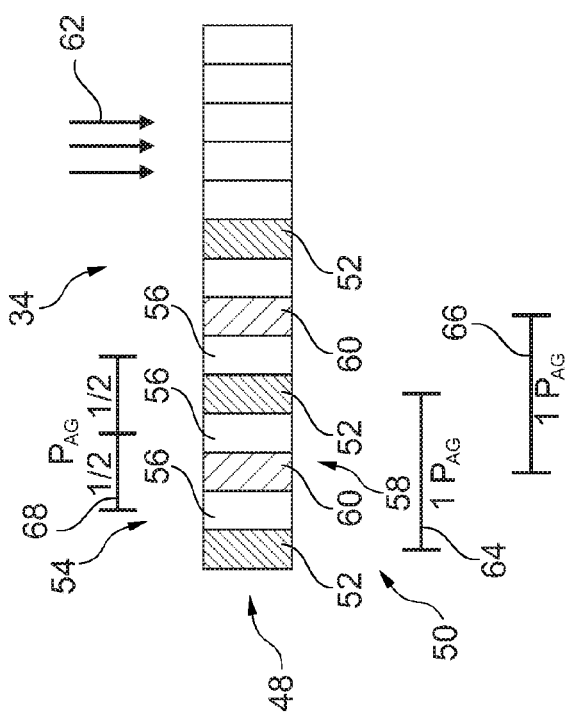
FIG. 4 shows a further embodiment of an analyzer grating according to the invention.

FIG. 3 and FIG. 4 schematically show two embodiments of the analyzer grating 34 for X-ray differential phase-contrast imaging. The analyzer grating 34 comprises an absorption structure 48 with a first plurality 50 of first areas 52 with a first X-ray attenuation. Further, a second plurality 54 of second areas 56 with a second X-ray attenuation is provided. The second X-ray attenuation is smaller than the first X-ray attenuation.

The first and second areas 52, 56 are arranged periodically in an alternating manner, wherein a third plurality 58 of third areas 60 is provided with a third X-ray attenuation, which lies in a range from the second X-ray attenuation to the first X-ray attenuation, and wherein every second of the first or second areas 52, 56 is replaced by one of the third areas 60.

The range of the third X-ray attenuation may include the first X-ray attenuation and the second X-ray attenuation. For example, the third X-ray attenuation is equal or smaller than the first X-ray attenuation. As a further example, the third X-ray attenuation is equal or larger than the second X-ray attenuation.

The term "area" may refer, for example, to different sections or fields along the cross-section of the absorption structure.

For example, the absorption structure is arranged with the periodic extension in a transverse direction to an X-ray radiation 62, indicated schematically only with three parallel arrows.

Further, the periodic repetition of the absorption structure 48 is indicated with reference numeral 64.

The first areas may be X-ray opaque and the second areas may be X-ray transparent.

According to a further aspect of the invention, the third areas may have an X-ray attenuation that is smaller than the X-ray attenuation of the first areas and larger than the X-ray attenuation of the second areas.

In general, the term "X-ray opaque" may comprise an X-ray attenuation of more than 70%, preferably more than 90%.

In general, the term "X-ray transparent" may comprise an X-ray attenuation of less than 40%, preferably less than 20%.

As can be seen, the third areas 60 can be provided with an analyzer grating pitch $p_{AG}$, which is indicated with reference numeral 66. As can be seen, the periodic repetition 64 is equal to the grating pitch $p_{AG}$ 66. The first or second areas can be provided with half of the analyzer grating pitch $p_{AG}$.

In FIG. 3, the second areas 56 are provided with ½ $p_{AG}$.

In FIG. 4, the first areas are provided with half of the analyzer grating pitch $p_{AG}$, which is indicated with reference numeral 68.

As mentioned above, the term "pitch" may relate to the repetition period of the area pattern.

For example, the areas of the first, second, and third pluralities 50, 54, 58 are provided with a pattern which is arranged periodically with the analyzer grating pitch $p_{AG}$.

As mentioned above, the first and second areas are arranged periodically in an alternating manner.

However, in FIG. 3, every second of the first areas 52 is replaced by one of the third areas 60.

However, in FIG. 4, every second of the second areas 56 is replaced by one of the third areas 60.

As will be described further below, the areas of the first, second, and third pluralities can be provided as alternating projections and recesses.

As also described further below, the areas of the first, second and third pluralities may also be provided as alternating bars and gaps.

It is noted that the term "alternating" comprises that two adjacent or neighbouring areas are of different area types, i.e., belonging to the first, the second, or the third plurality of areas.

According to a further exemplary embodiment, two of the group of first, second, and third pluralities are provided with a 4-stride 70, and one of the group of the first, second, and third pluralities is provided with a 2-stride 72, wherein the third plurality is provided with a 4-stride 70.

The terms "4-stride" and "2-stride" relate to the number of areas in one interval. For example, "4-stride" relates to four areas until the respective area type is repeated. The term "2-stride", for example, relates to two areas until the respective area is repeated. Instead, also the term "4-area-cycle" or "2-area-cycle" could be used. It is noted that the term "interval" does not automatically relate to the pitch or period of the grating.

Figure 5:
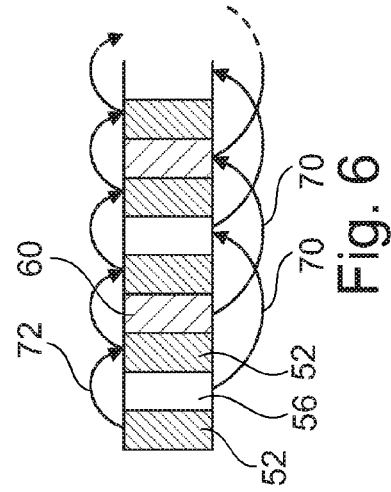
FIGS. 5 and 6 show further embodiments of an analyzer grating according to the invention.

For example, the embodiment in FIG. 5 shows the first plurality 50 with the first areas 52 provided with the 4-stride 70, as indicated with the arrows connecting equal area types. Further, the third plurality 58 is provided with a 4-stride 70, which is indicated by the arrows connecting the respective third areas 60. Still further, the second plurality 54 is provided with a 2-stride 72, which is indicated by the arrows connecting the respective second areas 56.

Figure 6:
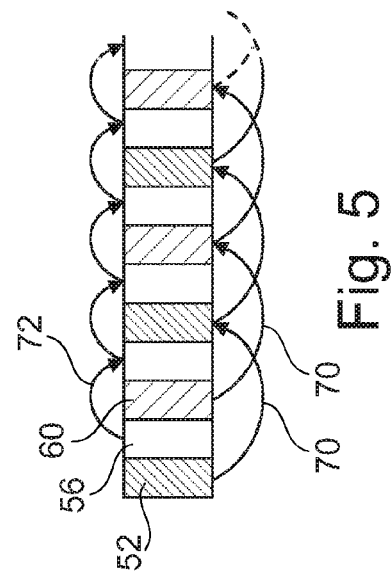

A further example is shown in FIG. 6, where the first plurality 50 with the first areas 52 is provided with a 2-stride 72. The second plurality 54 with the second areas 56 is provided with a 4-stride 70. The third plurality 58 with the third areas 60 is provided with a 4-stride 70, as is the case in FIG. 5.

According to a further aspect, a stride pattern comprises a rhythm of 1/2/1/3, wherein 1 refers to the first area type, 2 to the second area type and 3 to the third area type. For example, this results in a pattern of 1/2/1/3/1/2/1/3/1/2/1/3/1/2/1/3 . . . .

According to a further aspect, a stride pattern comprises a rhythm of 1/2/3/2, which, for example, results in a pattern of 1/2/3/2/1/2/3/2/1/2/3/2/1/2/3/2 . . . .

According to a further aspect, the first, second, and third areas are provided with equal area widths in the direction of the absorption structure.

According to a further exemplary embodiment, not further shown, the first, second, and third areas are provided with different area widths in the direction of the absorption structure, wherein the areas of a respective plurality have the same width.

Figure 7:
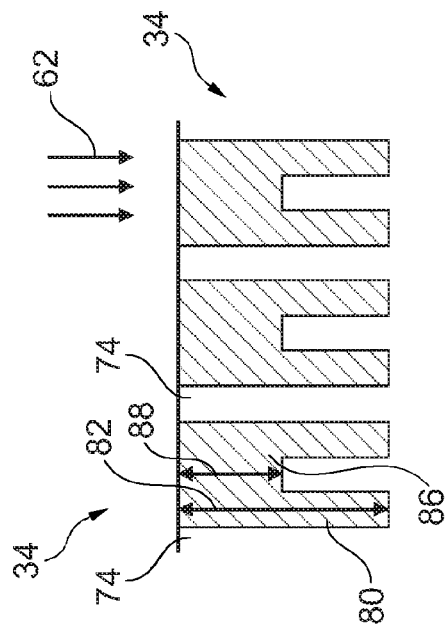
FIGS. 7, 8, 9, and 10 show further embodiments of an analyzer grating according to the invention.
Figure 8:
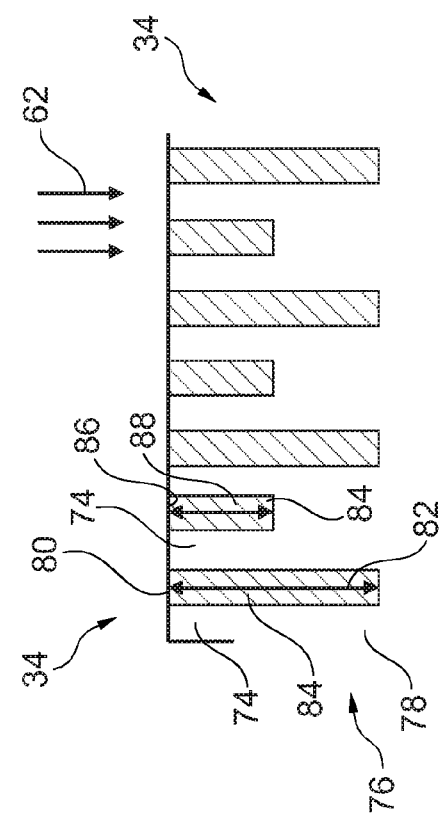

FIGS. 7 and 8 show further exemplary embodiments of an analyzer grating 34 according to the invention.

The second areas 56 may be provided as bars 74 of a comb-like structure 76, made from a structure material 78 with a low X-ray attenuation value. The first areas 52 are provided as first slits 80 with a first depth 82, which first slits are filled with a filling material 84 with a high X-ray attenuation value. The high attenuation value is larger than the low attenuation value. Further, the third areas 60 are provided as second slits 86 with a second depth 88 which is smaller than the first depth, wherein the second slits 86 are filled with the filling material 84, which is indicated by the same type of pattern.

In FIG. 7, the first slits 80 are provided between two bars 74, and the second slits 86 are arranged between two bars 74.

In FIG. 8, the bars 74 are provided between two first slits 80, and the second slits 86 are arranged between two first slits 80.

As can be seen in FIG. 8, the first and second slits 80, 86 can be provided as a common material structure in the range of their contacting surfaces.

Figure 9:
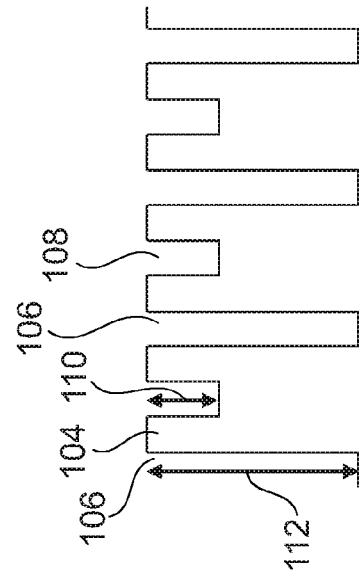
Figure 10:
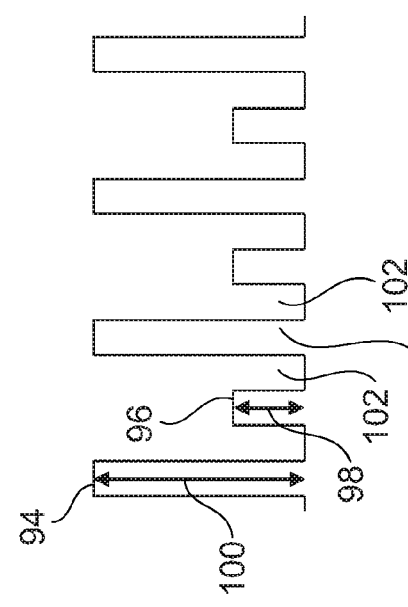

FIGS. 9 and 10 show further exemplary embodiments of an analyzer grating 34.

It is explicitly noted that throughout the figures and the description of the present application, the grating structures are shown with respect to their schematic arrangement and not with respect to scale or extension or number of different areas provided.

Contrary to the embodiments of FIGS. 7 and 8, the embodiments shown in FIGS. 9 and 10 comprise a comb-like structure 90 made from a structure material 92 with a high attenuation value.

In the exemplary embodiment of FIG. 9, the first areas 52 are provided as first bars 94 of the comb-like structure 90. The third areas 60 are provided as second bars 96, wherein the first bars 94 and the second bars 96 are made from the structure material 92. The second bars 96 are provided with a height 98 which is smaller than a height 100 of the first bars 94. The second areas 56 are provided as slits 102 between the bars 94, 96.

The third areas 60 may be provided as partly cut bars.

In FIG. 10, the first areas 52 are provided as bars 104 of the comb-like structure made from the structure material with the high X-ray attenuation value. The second areas 56 are provided as first slits 106 between the bars. The third areas are provided as second slits 108 with a depth 110 which is smaller than the depth 112 of the first slits 106.

The second areas are provided as grooves between the bars. They also may be provided as gaps between the bars.

Further, the third areas are provided as partly filled gaps or grooves.

According to a further exemplary embodiment, the high attenuation value comprises an X-ray attenuation of at least 70%, preferable at least 90%.

Further, examples of FIGS. 9 and 10 may be arranged such that the slits are not filled with material or with a material with an X-ray transparent material, or at least a material with a low X-ray attenuation value.

According to a further exemplary embodiment, shown in FIG. 11, the analyzer grating 34 may be provided with a comb-like structure 114 made from a structure material 116 with a low X-ray attenuation value, for example as in FIGS. 7 and 8. The first areas 52 are provided as slits 118 filled with a filling material 120 with a high X-ray attenuation value. The high attenuation value is larger than the low attenuation value, as already mentioned above.

Since the third X-ray attenuation of the third areas 60 belonging to the third plurality 58 lies in a range from the second X-ray attenuation to the first X-ray attenuation, it is also possible to provide the second areas 56 similar to the third areas 60. In the example shown in FIG. 11, a broader bar 122 is shown provided between the filled gaps 118. The broader bar 122 comprises a third area 60 arranged between two second areas 56, which is indicated by dotted lines.

FIG. 12 shows a further comb-like structure 124 made from a structure material 126 with a low X-ray attenuation value. The second areas 56 are provided as bars 128. A broader gap or slit 130 is arranged between two bars 128. The broader slit 130 comprises a third area 60 arranged between two first areas 52, which is indicated with dotted lines.

In other words, the example shown in FIG. 11 comprises second areas and third areas 60 with the same X-ray attenuation. The example shown in FIG. 12 shows the first areas 52 and the third areas 60 with the same X-ray attenuation.

FIG. 13 shows an exemplary embodiment of a phase grating 132 for X-ray differential phase-contrast imaging. The phase grating 132 comprises a deflection structure 134 with a fourth plurality 136 of fourth areas 138 and a fifth plurality 140 of fifth areas 142. The fourth and fifth areas 136, 142 are arranged periodically in an alternating manner. The fourth areas 138 are provided to change the phase and/or amplitude of an X-ray radiation 62 and the fifth 142 are provided to modulate the amplitude of the X-ray radiation 62.

For example, the phase grating may be provided as a comb-like structure with projecting bars and gaps between the bars, wherein the fourth areas are provided as the bars and wherein the fifth areas are provided as the connecting areas between the bars.

According to an exemplary embodiment, the phase grating 132 is provided as a comb-like structure with a structure material which is heavier than silicon, wherein the atomic number and/or the density of the structure material is larger than the atomic number and/or the density of silicon.

For example, the structure material can be at least 10% heavier than silicon.

The areas of the fourth and fifth pluralities 136, 140 are provided with a phase grating pitch $p_{PG}$, indicated with numeral 144.

According to an aspect of the invention, the phase grating pitch $p_{PG}$ matches the analyzer grating pitch $p_{AG}$ or is in accordance with the analyzer grating pitch $p_{AG}$.

For example, in case of parallel X-ray propagation, the phase grating pitch is equal to the analyzer grating pitch, i.e. $p_{PG}=p_{AG}$.

As a further example, in case of fan-shaped X-ray propagation, the analyzer grating pitch is in accordance with the phase grating pitch depending on the magnification relating to the distance of the two gratings and the propagation fan-angle.

According to an aspect of the invention, the phase grating can have a smaller aspect ratio than the usual gratings due to heavier material used for the grating structure. Thus, it is also possible to provide a phase grating with a larger acceptance angle than the usual gratings. The aspect ratio and also the acceptance angle depend on the relationship between the energy of the X-ray radiation and the material used for the grating. The acceptance angle relates to the range in which X-ray beams can be effectively provided to the phase grating in order to pass the phase grating towards the analyzer grating.

Figure 14:
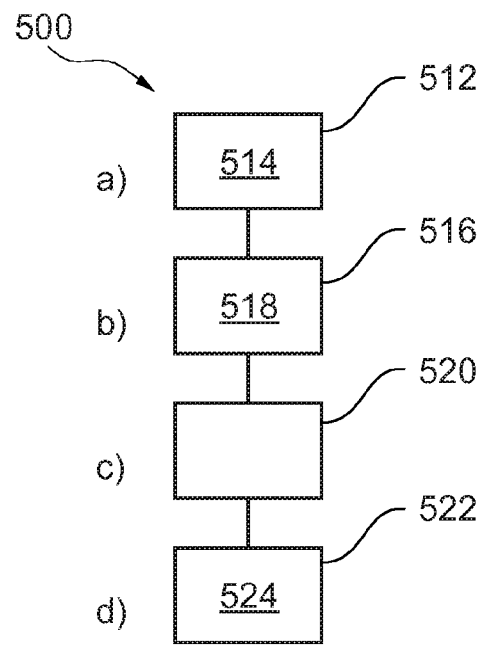
FIG. 14 shows an exemplary embodiment of a method according to the invention.

In the following, an exemplary embodiment of the method 500 for differential phase-contrast imaging will be described with reference to FIG. 14. The method 500 comprises the following steps. In a first application step 512, at least partly coherent X-ray radiation 514 is applied to an object of interest. Further, in a second application step 516, the X-ray radiation which passes the object is applied to a phase grating recombining 518 the splitted beams in an analyzer plane. In a third application step 520, the recombined beams are applied to an analyzer grating arranged in the analyzer plane. In a recording step 522, raw image data is recorded with a sensor while stepping 524 the analyzer grating.

The phase grating in the second application step 516 is provided with a fourth plurality of fourth areas and the fifth plurality of fifth areas, wherein the fourth areas are provided to change the phase and/or amplitude of an X-ray radiation, and wherein the fourth and fifth areas are arranged periodically in an alternating manner with a phase grating pitch $p_{PG}$. Further, in the second application step 516, a subharmonic in the interference pattern is provided at the position of the analyzer grating. The analyzer grating in the recording step 522 as well as the stepping step 524 is an analyzer grating according to one of the above-mentioned embodiments. Further, the stepping step 524 comprises stepping the analyzer grating transversely over at least a full modulation period of the X-ray radiation passing the phase grating.

For example, in case of parallel X-ray propagation, the phase grating and/or the analyzer grating are adapted to be stepped in a manner transverse to the deflection structure at least over a full phase grating pitch $p_{PG}$.

As a further example, in case of fan-shaped X-ray propagation, the phase grating and/or the analyzer grating are adapted to be stepped in a manner transverse to the deflection structure at least over a magnified full phase grating pitch $p_{PG}$, which magnification is depending on the distance and the propagation fan-angle.

According to a further exemplary embodiment of the method, the phase grating in the second application step 516 is a phase grating according to one of the above-mentioned and described embodiments.

According to a further example of the method, the first application step 512 is also referred to as step a), the second application 516 as step b), the third application step 520 as step c), and the recording step 522 as step d).

Figure 15:
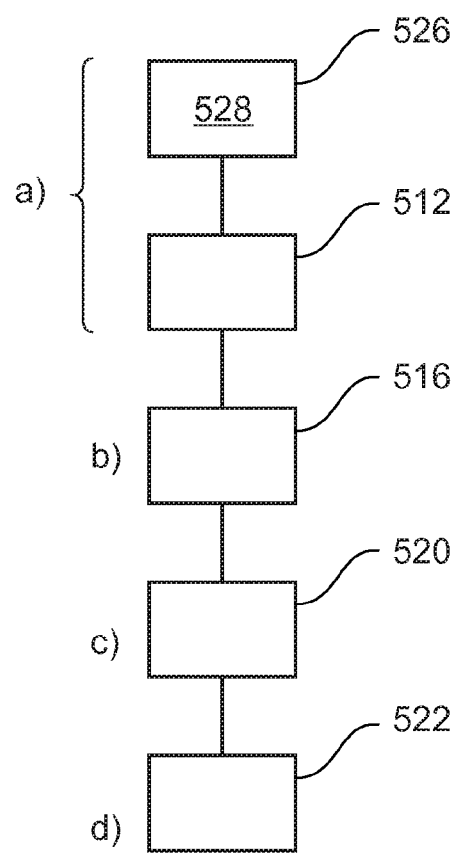
FIG. 15 shows a further embodiment of a method according to the invention.

According to a further exemplary embodiment, shown in FIG. 15, step a) comprises an initial application step 526 in which X-ray radiation of a conventional X-ray source, i.e. where the polychromatic X-ray radiation spectrum is applied to a source grating splitting 528 the radiation, wherein the at least partly coherent X-ray radiation is generated.

In the following, further aspects of the invention will be described with reference to FIGS. 16 to 19. In FIGS. 16 to 19; also a comparison is made between a standard differential phase-contrast imaging setup with a pure phase grating and the results of the analyzer grating according to the invention. The pure phase grating situation is shown in the left halves of FIGS. 16 to 19, also indicated with an a) above the respective column. The result and effect of the analyzer grating according to the invention is shown in the right halves of the FIGS. 16 to 19, also indicated with a letter b) above the respective column.

Figure 16:
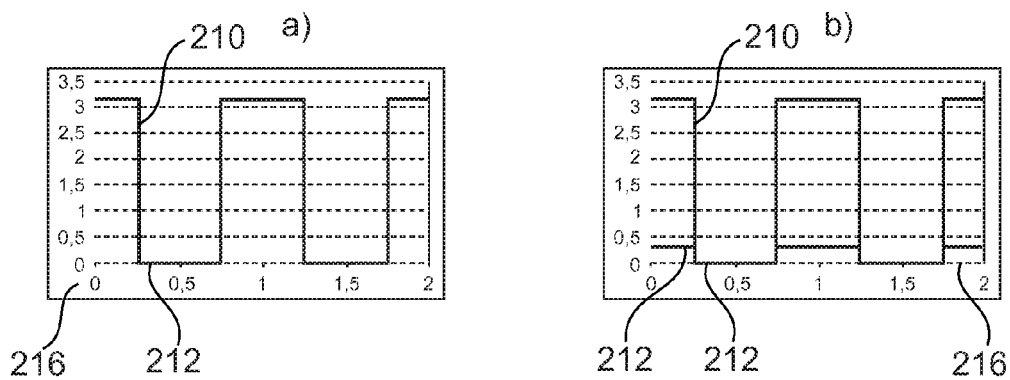
FIGS. 16 to 19 show further aspects of embodiments according to the invention.

FIG. 16 shows the phase shift 210 and the transmission 212 of a phase grating G1 over two grating pitches. As can be seen in the standard setup in column a), the transmission 212 is a through line, i.e. no effect with regard to the transmission is provided. Contrary to this, the present invention provides additional intensity modulation of the beam, as can be seen from the stepped transmission line 212 in FIG. 16b). This intensity modulation is provided in addition to the phase modulation 210.

Figure 17:
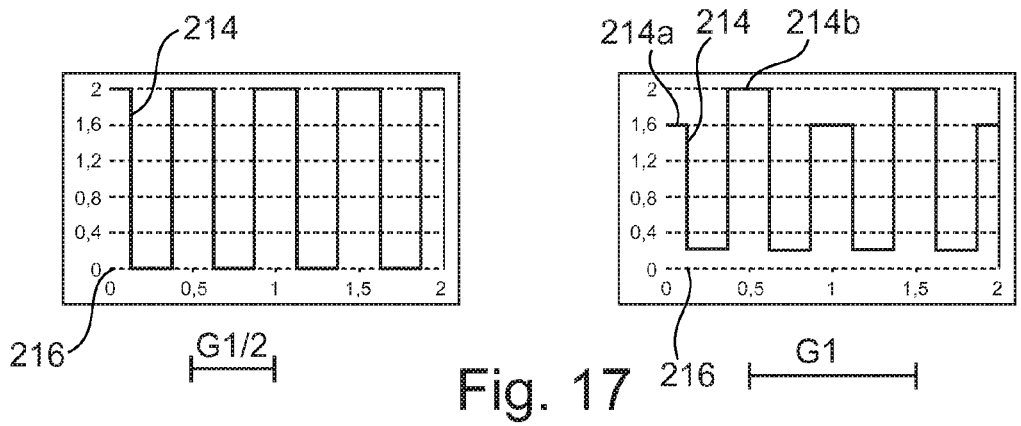

After the beam has traveled to the position of G2, as indicated in FIG. 17, every other intensity maximum is damped, which can be seen from an intensity profile 214 at G2 shown in FIG. 17. In FIG. 17a), i.e. for the standard setup, the intensity maxima are the same. Compared to this, the present invention provides a different curve for the intensity profile, namely with lower maxima 214a and higher maxima 214b).

Figure 18:
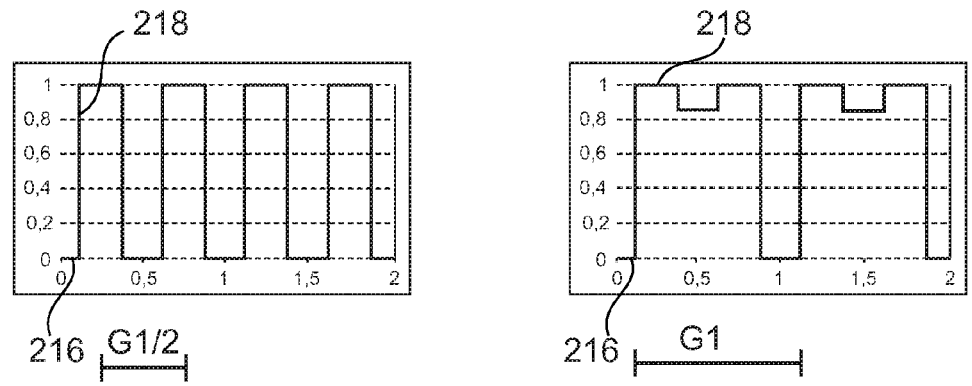
Figure 19:
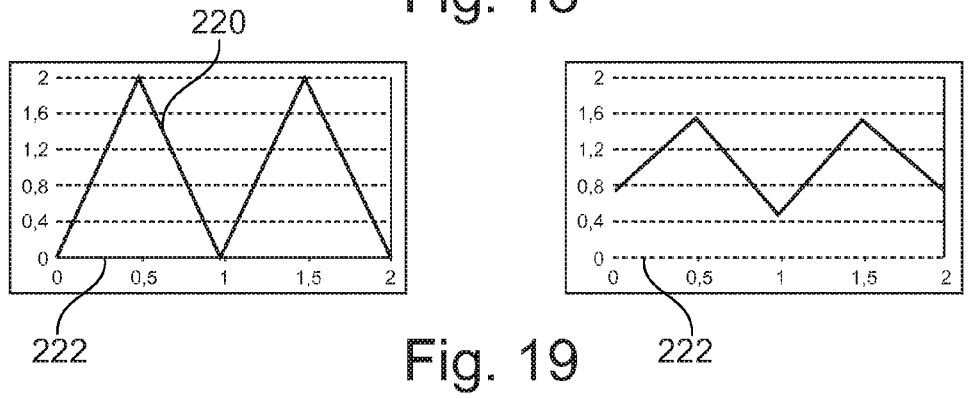

In other words, the periodicity of the signal in FIG. 17a) is half of G1, which can easily be retrieved by the X-axis in FIGS. 16, 17, and 18 showing a spatial coordinate 216.

Contrary to the result of the standard setup in FIG. 17a), the result of the present invention as shown in FIG. 17b) shows a periodicity of the signal to be G1.

In a standard setup with an analyzer grating that demodulates the beam intensity with a periodicity of ½G1, the change in the intensity pattern is invisible since the detector averages over a couple of maxima. However, if the transmission of the analyzer grating is also changed such that it has a periodicity of G1, then the change becomes visible as illustrated in FIG. 19b). Basically, what happens in the example shown is that the maxima of the detector signal are the same, since this is related to a position of the analyzer grating where both maxima are not attenuated, but the depth of the minima differs, since then the maxima are attenuated differently. Thereby, the dynamic range of the phase gradient measurement can be increased by a factor of 2: the dynamic range of the standard setup is limited by the fact that if the gradient of phase front becomes that large that the intensity profile of the beam at the position of G2, which is shown in FIG. 17, is shifted by ½G1, then the intensity profile cannot be distinguished from the case of a no-shift. Back to FIG. 17, the graph in FIG. 17b) shows the resulting intensity variation at the position of G2, i.e., after the X-ray beam has traveled along the optical axis over one fractional Talbot distance.

FIG. 18 shows the transmission of the analyzer grating, indicated with a further graph 218. As can be seen, the analyzer grating G2 according to the standard setup in FIG. 18a) has a periodicity of ½G1, whereas the transmission 218 of G2 according to the present invention has a periodicity of G1.

As mentioned above, FIG. 19 shows a measured intensity 220 as a function of the grid position. It is noted that the X-axis of FIG. 19, indicated with reference numeral 222, relates to the relative position of grating G2 with respect to the intensity profile. The range of X in the FIGS. 19a) and 19b) is only one grating pitch and the position X=0 relates to the position as indicated in FIGS. 17 and 18.

It is further noted that the transmission of G1 shown in FIG. 18b) is only shown as an example and can also be provided according to one of the above described analyzer grating structures with different attenuation.

FIG. 20, once again, shows a standard setup with a pure phase grating with a pitch G1. The grating is indicated with a grating structure 224. Further, two stepping positions 226 and 228 for the analyzer grating are shown in the two rows below the phase grating structure 224. The analyzer grating structure is schematically indicated with an analyzer grating structure 230.

The resulting measured intensity is shown in FIG. 21 with an intensity curve 232, which measured intensity is measured behind grating G2, i.e. behind the analyzer grating. As indicated with arrows 234 as well as 236, the position 226 relates to the starting point of the curve, whereas the maximum of the curve, indicated with reference numeral 238 relates to the position 228.

FIG. 22 shows an intensity 240 at a phase grating G1 according to the invention. As can be seen, the intensity has a periodicity which is twice as large as the one of the standard setup shown in FIG. 20. This is indicated with the reference numeral 242 indicating P2/2.

Below the intensity curve 240, the different stepping positions for an analyzer grating according to the invention are shown, namely for a first position 244, a second position 246, and a third position 248. In position 244, the analyzer grating 34 is provided at position 1 of the X-axis shown in FIGS. 16 to 18. In the second position, 246, the position is X=2, and the third position 248 relates to the position of X=3.

In the first position 244, no transmission is provided. Further, as indicated, in a first segment 250, 100% attenuation is provided, in a second segment 252, 50% attenuation is provided, and in a third segment 254, 100% attenuation is provided, and in a fourth segment 256, 0% attenuation is provided.

As can be seen from the second position 246, 100% of the high intensity and 50% of the low intensity can pass the analyzer grating according to the invention.

With respect to the third position 248, 50% of the high intensity and 100% of the low intensity can pass the analyzer grating.

This leads to the measured intensity curve 248, measured behind the analyzer grating G2, as shown in FIG. 23.

FIG. 24 shows a further intensity curve 260 in the upper row for zero gradient, and a still further intensity curve 262, showing the dynamic range extension. The distinction of the two curves cannot be achieved with a standard analyzer grating, but with an analyzer grating according to the present invention, as described above.

In another exemplary embodiment of the present invention (not shown), a computer program or a computer program element is provided i.e. characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above. According to a further exemplary embodiment of the present invention (not shown), a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

The invention claimed is:

1. An analyzer grating for X-ray differential phase-contrast imaging, comprising an absorption structure with:
   a first plurality of first areas with a first X-ray attenuation; and
   a second plurality of second areas with a second X-ray attenuation;
   wherein the second X-ray attenuation is smaller than the first X-ray attenuation;
   wherein the first and second areas are arranged periodically in an alternating manner;
   and wherein a third plurality of third areas is provided with a third X-ray attenuation, which lies in a range from the second X-ray attenuation to the first X-ray attenuation; and
   wherein every second of the first or second areas is replaced by one of the third areas.

2. The analyzer grating according to claim 1,
   wherein the first areas are X-ray opaque;
   wherein the second areas are X-ray transparent;
   wherein the third areas have an X-ray attenuation that is smaller than the X-ray attenuation of the first areas and larger than the X-ray attenuation of the second areas.

3. The analyzer grating according to claim 1, wherein two of the group of first, second and third pluralities are provided with a 4-stride, and one of the group of the first and second pluralities is provided with a 2-stride; wherein the third plurality is provided with a 4-stride.

4. The analyzer grating according to claim 1, wherein the second areas are provided as bars of a comb-like structure made from a structure material with a low X-ray attenuation value; wherein the first areas are provided as first slits with a first depth, which first slits are filled with a filling material with a high X-ray attenuation value; wherein the high attenuation value is larger than the low attenuation value; and wherein the third areas are provided as second slits with a second depth which is smaller than the first depth; wherein the second slits are filled with the filling material.

5. A grating arrangement for X-ray differential phase-contrast imaging, comprising:
   the analyzer grating according to claim 1; and
   a deflection structure disposed in front of the analyzer grating, the deflection structure including:
   a fourth plurality of fourth areas; and
   a fifth plurality of fifth areas;
   wherein the fourth and fifth areas are arranged periodically in an alternating manner;

wherein the fourth areas are provided to change the phase and/or amplitude of an X-ray radiation; and
wherein the fifth areas are provided to modulate the amplitude of the X-ray radiation.

6. The grating arrangement according to claim 5, wherein the phase grating is provided as a comb-like structure with a structure material which is heavier than silicon; wherein the atomic number and/or the density of the structure material is larger than the atomic number and/or the density of silicon.

7. A detector arrangement of an X-ray system for generating differential phase-contrast images of an object comprising:
   a phase grating with a phase grating pitch $p_{PG}$;
   an analyzer grating; and
   a detector with a sensor adapted to record intensity variations of an X-ray radiation;
   wherein in radiation direction, the analyzer grating is arranged behind the phase grating, and the detector is arranged behind the analyzer grating;
   wherein the phase grating is provided with:
      a fourth plurality of fourth areas; and
      a fifth plurality of fifth areas;
      wherein the fourth areas are provided to change the phase and/or amplitude of an X-ray radiation;
      wherein the fourth and fifth areas are arranged periodically in an alternating manner with a phase grating pitch $p_{PG}$;
   wherein the analyzer grating is provided according to claim 1; and
   wherein the phase grating and/or the analyzer grating are adapted to be stepped in a manner transverse to the deflection structure at least over a full modulation period of the X-ray radiation passing the phase grating.

8. The detector arrangement according to claim 7, wherein the analyzer grating pitch $p_{AG}$ matches the phase grating pitch $p_{PG}$.

9. An X-ray image acquisition device for generating differential phase-contrast images of an object, with
   an X-ray source;
   a phase grating;
   an analyzer grating; and
   a detector;
   wherein the X-ray source generates X-ray radiation;
   wherein the X-ray image acquisition device is adapted to provide an X-ray beam with sufficient coherence, so that interference can be observed at the location of the analyzer grating; and
   wherein the phase grating, the analyzer grating and the detector are provided as a detector arrangement according to claim 7.

10. An X-ray imaging system for differential phase contrast imaging, comprising:
    an X-ray image acquisition device for generating differential phase-contrast images of an object according to claim 9,
    a processing unit; and
    an interface unit;
    wherein the processing unit is adapted to control the X-ray source as well as the phase-stepping of the analyzer grating and/or the phase grating; and
    wherein the interface unit is adapted to provide the detected raw image data to the processing unit.

11. A method for differential phase contrast imaging, comprising the steps of:
    a) applying at least partly coherent X-ray radiation to an object of interest;
    b) applying the X-ray radiation passing the object to a phase grating recombining the splitted beams in an analyzer plane;
    c) applying the recombined beams to an analyzer grating arranged in the analyzer plane;
    d) recording raw image data with a sensor while stepping the analyzer grating;
    wherein the phase grating in step b) is provided with:
       a fourth plurality of fourth areas; and
       a fifth plurality of fifth areas;
       wherein the fourth areas are provided to change the phase and/or amplitude of an X-ray radiation; and
       wherein the fourth and fifth areas are arranged periodically in an alternating manner with a phase grating pitch $p_{PG}$;
    wherein in step b) a subharmonic in the interference pattern at the position of the analyzer grating is provided;
    wherein the analyzer grating in step d) is an analyzer grating according to claim 1; and
    wherein step d) comprises stepping the analyzer grating transversely over at least a full modulation period of the X-ray radiation passing the phase grating.

12. The method according to claim 11, wherein step a) comprises applying X-ray radiation of a conventional X-ray source to a source grating splitting the radiation, wherein the at least partly coherent X-ray radiation is generated.

13. A non-transitory computer-readable medium having thereon instructions which when executed on a computer cause an X-ray system including the detector arrangement according to claim 7 to perform a method of differential phase contrast imaging, comprising the steps of:
    a) applying at least partly coherent X-ray radiation to an object of interest;
    b) applying the X-ray radiation passing the object to the phase grating recombining the splitted beams in an analyzer plane;
    c) applying the recombined beams to the analyzer grating arranged in the analyzer plane;
    d) recording raw image data with a sensor while stepping the analyzer grating;
    wherein step d) comprises stepping the analyzer grating transversely over at least a full modulation period of the X-ray radiation passing the phase grating.

* * * * *